United States Patent
Ichi et al.

(10) Patent No.: US 9,956,334 B2
(45) Date of Patent: May 1, 2018

(54) SEPARATION MEMBRANE FOR BLOOD PROCESSING AND BLOOD PROCESSING APPARATUS HAVING THE MEMBRANE INSTALLED THEREIN

(71) Applicant: ASAHI KASEI MEDICAL CO., LTD., Tokyo (JP)

(72) Inventors: Takahiro Ichi, Tokyo (JP); Toshinori Koizumi, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 311 days.

(21) Appl. No.: 14/355,641

(22) PCT Filed: Nov. 2, 2012

(86) PCT No.: PCT/JP2012/078461
§ 371 (c)(1),
(2) Date: May 1, 2014

(87) PCT Pub. No.: WO2013/065819
PCT Pub. Date: May 10, 2013

(65) Prior Publication Data
US 2014/0284261 A1   Sep. 25, 2014

(30) Foreign Application Priority Data
Nov. 4, 2011   (JP) .................. 2011-242260

(51) Int. Cl.
| | |
|---|---|
| B01D 39/00 | (2006.01) |
| B01D 39/14 | (2006.01) |
| B01D 71/06 | (2006.01) |
| A61M 1/16 | (2006.01) |
| B01D 71/68 | (2006.01) |
| B01D 65/02 | (2006.01) |
| B01D 69/08 | (2006.01) |
| B01D 71/62 | (2006.01) |
| B01D 69/14 | (2006.01) |
| A61M 1/36 | (2006.01) |
| C02F 1/50 | (2006.01) |
| B01D 24/00 | (2006.01) |

(52) U.S. Cl.
CPC ............ *A61M 1/16* (2013.01); *A61M 1/3644* (2014.02); *B01D 65/022* (2013.01); *B01D 69/08* (2013.01); *B01D 69/087* (2013.01); *B01D 69/141* (2013.01); *B01D 71/62* (2013.01); *B01D 71/68* (2013.01); *A61M 1/3643* (2013.01)

(58) Field of Classification Search
None
See application file for complete search history.

(56) References Cited

U.S. PATENT DOCUMENTS

| | | | |
|---|---|---|---|
| 6,432,309 B1 | 8/2002 | Fuke et al. | |
| 6,977,044 B1* | 12/2005 | Oishi .................. | A61M 1/3633 210/500.42 |
| 2003/0094409 A1* | 5/2003 | Minegishi ............ | B01D 61/145 210/500.23 |
| 2006/0108288 A1 | 5/2006 | Oishi | |
| 2008/0087599 A1* | 4/2008 | Mabuchi ................. | A61L 2/087 210/500.23 |
| 2009/0078641 A1* | 3/2009 | Monden ................. | B01D 69/08 210/321.6 |
| 2009/0314708 A1* | 12/2009 | Yeom ..................... | B01D 61/36 210/500.23 |
| 2010/0133170 A1 | 6/2010 | Satoh et al. | |
| 2011/0017654 A1* | 1/2011 | Ueno ..................... | B01D 63/02 210/321.6 |

FOREIGN PATENT DOCUMENTS

| | | | | |
|---|---|---|---|---|
| CN | 1684727 A | 10/2005 | | |
| EP | 1230940 A1 | 8/2002 | | |
| EP | 2529769 A1 | 12/2012 | | |
| JP | 2005-066389 A | 3/2005 | | |
| JP | 2007-295987 A | 11/2007 | | |
| JP | 2007295987 A | * 11/2007 | | |
| JP | 2008-290009 A | 12/2008 | | |
| JP | 2009-202134 A | 9/2009 | | |
| JP | 2009-262147 A | 12/2009 | | |
| JP | 2010-104984 A | 5/2010 | | |
| JP | 2011-072987 A | 4/2011 | | |
| JP | 2011-078974 A | 4/2011 | | |
| JP | 2011-092928 A | 5/2011 | | |
| WO | 2008-032400 A1 | 3/2008 | | |
| WO | WO 2009123088 A1 * | 10/2009 | ............ | B01D 63/02 |
| WO | 2011-090197 A | 7/2011 | | |

OTHER PUBLICATIONS

Machine translation of Akamatsu et al. (JP 2007295987 A), pp. 1-9.*
International search report for application No. PCT/JP2012/078461, dated Jan. 22, 2013.
Office Action issued for Taiwanese application No. 101140885, dated Apr. 15, 2014.
Search Report dated Mar. 24, 2015 for EP12845111.9.

* cited by examiner

*Primary Examiner* — Clare M Perrin
(74) *Attorney, Agent, or Firm* — Greenblum & Bernstein, P.L.C.

(57) ABSTRACT

The present invention provides a separation membrane for blood processing, comprising a polysulfone polymer, a hydrophilic polymer and a polymer having a hydroxy group in a side chain and having a solubility of 0.5 g or less in water (100 g) at 20° C., in which the content of the polymer falls within a specific range, and a blood processing apparatus having the membrane installed therein.

13 Claims, No Drawings

SEPARATION MEMBRANE FOR BLOOD PROCESSING AND BLOOD PROCESSING APPARATUS HAVING THE MEMBRANE INSTALLED THEREIN

TECHNICAL FIELD

The present invention relates to a separation membrane for blood processing and a blood processing apparatus having the separation membrane installed therein.

BACKGROUND ART

As a therapeutic approach for improving symptoms by removing from disease agents and toxic waste materials accumulated in blood due to various causes, an extracorporeal-circulation blood purification therapy has been widely applied.

In the extracorporeal-circulation blood purification therapy, a blood processing apparatus is used. Examples of the blood processing apparatus include a hemodialyzer, a hemofilter, a blood fractionator and a plasma separator. The separation membrane for blood processing is a separation membrane to be charged in a blood processing apparatus. At present, majority of blood processing apparatuses is occupied by a hollow fiber membrane-based blood processing apparatus.

As a membrane base material for the separation membrane for blood processing, a base material mainly comprising a polymer, such as a cellulose polymer, a cellulose acetate polymer, a polyamide polymer, a polyolefin polymer, a polyacrylonitrile polymer and a polysulfone polymer, has been used. Among them, the polysulfone polymer has been increasingly used as a base material for a separation membrane for blood processing in recent years, since it is excellent in membrane-formability in addition to biological safety and chemical stability; and a wide range of membranes can be designed to have a variety of permeability and membrane structures. These polymers are characterized in that they have excellent resistances against radiation, heating and chemical agents such as acids or alkalis; however, since they are hydrophobic polymers, these polymers lack affinity for blood if they are used as they are.

As a hydrophilizing agent for a separation membrane for blood processing, a hydrophilic polymer having a small stimulus on blood is used. Examples of such a hydrophilic polymer include a polyvinylpyrrolidone, a polyvinyl alcohol and a polyethylene glycol.

Patent Literature 1 discloses that at least one of a polyalkylene oxide including polyethylene glycol, a polyvinylpyrrolidone, a polyvinyl alcohol, a poly(hydroxyethyl methacrylate), a polyacrylamide and a polyethylene imine is added for imparting hydrophilicity; and that incorporating such a hydrophilic polymer in the membrane hydrophilizes the surface of the membrane and provide an effect of suppressing adsorption of proteins to the membrane.

Patent Literatures 2 to 5 disclose, for further improving blood compatibility, methods for effectively suppressing adhesion of proteins and platelets by controlling balance between hydrophilicity and hydrophobicity by using a membrane having a vinylpyrrolidone unit and a hydrophobicity unit other than a polysulfone unit.

Even in such a separation membrane for blood processing prepared based on creative ideas as described above, initial performance may decrease or disappear with the passage of time. For example, a separation membrane is degraded by oxygen, temperature and light, etc. during transportation and storage. Storage for a long period may cause, even at about room temperature and with care, a chemical change more than a little in a separation membrane of a blood processing apparatus. In addition, during transportation, a separation membrane also has the potential to be exposed to high temperature.

If a separation membrane chemically changes, it is easily estimated that blood compatibility present in the beginning of storage reduces and a hydrophilic polymer is decomposed, with the result that the amount of eluted substances from the separation membrane increases. As a method for suppressing a chemical change of a separation membrane, Patent Literature 6 discloses that considering water content of the separation membrane, airtightness of a packaging material and the atmosphere within a package, a blood processing apparatus is kept under deoxidation conditions by packaging the apparatus together with a deoxidant, thereby reducing a change in amount of eluted substances from the separation membrane for a long time period.

CITATION LIST

Patent Literature

Patent Literature 1: Japanese Patent Laid-Open No. 2009-202134
Patent Literature 2: Japanese Patent Laid-Open No. 2009-262147
Patent Literature 3: Japanese Patent Laid-Open No. 2010
Patent Literature 4: Japanese Patent Laid-Open No. 2011-72987
Patent Literature 5: Japanese Patent Laid-Open No. 2011-78974
Patent Literature 6: Japanese Patent Laid-Open No. 2005-66389

SUMMARY OF INVENTION

Problems to be Solved by the Invention

Even if a deoxidant is packaged together with a blood processing apparatus, if a pinhole is formed in the package, the atmosphere within the package is not deoxidized, with the result that the quality of a separation membrane decreases. In this case, the integrity of the packaging must be strictly controlled. Accordingly, a special packaging material must be used in some cases. However, a cost for using and producing such a special packaging material is high. For this reason, it is difficult to attain the integrity of the packaging by use of a deoxidant or the like.

In the circumstances, it has been desired to develop a separation membrane having more excellent blood compatibility, which membrane is endowed with hydrophilicity, as well as the capability of suppressing protein adsorption.

Based on the studies of the present inventors, it was elucidated that the performance of a separation membrane decreases not only by the passage of time during storage but also by irradiation sterilization. When radicals are generated by irradiation, the decomposition reaction and crosslinking reaction of a hydrophilic polymer proceed and the surface of the separation membrane becomes hydrophobic. As a result, adsorption of proteins and adhesion of blood cell components proceed during blood processing, thereby blood compatibility significantly reduces. In addition, elution of decomposition products of the hydrophilic polymer becomes a problem.

Accordingly, a means for protecting the hydrophilic polymer from the decomposition reaction and crosslinking reaction caused by radical generation is required.

Radicals are also generated by oxygen, heat and light during sterilization or storage. If the decomposition reaction and crosslinking reaction of a hydrophilic polymer added to a separation membrane proceed by radicals, the surface of the separation membrane becomes hydrophobic. In addition, decomposition products elute off. If the surface of the separation membrane becomes hydrophobic, protein adsorption and adhesion of blood cell components proceed during blood processing, with the result that blood compatibility significantly reduces. It is further concerned that the decomposition products may elute into blood.

The present invention was made with a view to solving these problems and concerns and is directed to providing a separation membrane for blood processing, having high blood compatibility, storage stability and membrane performance that rarely deteriorates even if irradiation sterilization treatment is applied, and providing a blood processing apparatus having such a membrane installed therein. The present invention is also directed to providing a separation membrane for blood processing, having satisfactory air-bleeding during priming treatment of the blood processing membrane and providing a blood processing apparatus having such a membrane installed therein.

Means for Solving the Problem

The present inventors made intensive studies with a view to attaining the aforementioned objects. As a result, they found that if a polymer having a hydroxy group in a side chain and having a solubility of 0.5 g or less in 100 g of water at 20° C. is added to a conventional membrane base material comprising a polysulfone polymer and a hydrophilic polymer so as to be locally present in the functional separation surface, a separation membrane having a high blood compatibility and storage stability and membrane performance that rarely deteriorates even if irradiation sterilization treatment is applied; and also having satisfactory air-bleeding during priming treatment of separation membrane for blood processing, can be obtained. Based on the finding, the present invention was accomplished. More specifically, the present invention is as follows.

(1) A separation membrane for blood processing comprising a polysulfone polymer, a hydrophilic polymer and a polymer having a hydroxy group in a side chain and having a solubility of 0.5 g or less in water (100 g) at 20° C., wherein the content of the polymer in the separation membrane is 0.01 to 0.6 mass %;

the average concentration of the polymer in a functional separation surface of the separation membrane is 20 mass % or more, and a maximum value and a minimum value of the polymer concentration in the functional separation surface fall within the range of (the average concentration of the polymer in the functional separation surface)±15%; and the average concentration of the polymer in the functional separation surface relative to the content of the polymer in the separation membrane is 100 times or more.

(2) The separation membrane for blood processing according to (1), wherein the separation membrane is sterilized by radiation.

(3) The separation membrane for blood processing according to (1) or (2), wherein the hydrophilic polymer is polyvinylpyrrolidone.

(4) The separation membrane for blood processing according to any of (1) to (3), wherein the polysulfone polymer is at least one selected from the group consisting of polysulfone, polyethersulfone, polyphenylenesulfone, polyarylethersulfone and a copolymer of these.

(5) A blood processing apparatus in which the separation membrane for blood processing according to any of (1) to (4) is installed.

Advantageous Effects of Invention

The separation membrane for blood processing and a separator having the membrane installed therein according to the present invention are superior not only in substance removal performance but also in blood compatibility and has high storage stability and an effect of maintaining membrane performance even if irradiation sterilization treatment is applied; and also an effect of having a satisfactory air-bleeding during priming of the separation membrane for blood processing.

MODE FOR CARRYING OUT THE INVENTION

Now, embodiments for carrying out the present invention (hereinafter, referred to as "the embodiment") will be more specifically described below. Note that the present invention is not limited to the following embodiments and can be modified in various ways and carried out within the gist thereof.

The separation membrane for blood processing according to the embodiment (hereinafter, sometimes simply described as "the separation membrane") is a separation membrane comprising a polysulfone polymer, a hydrophilic polymer and a polymer having a hydroxy group in a side chain and having a solubility of 0.5 g or less in water (100 g) at 20° C.

The separation membrane of the embodiment contains a polysulfone polymer as a main constituent, and is also required to contain a hydrophilic polymer as a hydrophilizing agent for the separation membrane. Owing to the presence of the hydrophilic polymer, adsorption of proteins to the separation membrane can be suppressed, with the result that a separation membrane having high biocompatibility can be obtained.

In the separation membrane of the embodiment, it is necessary to further contain a polymer having a hydroxy group in a side chain and having a solubility of 0.5 g or less in water (100 g) at 20° C. (hereinafter, sometimes simply described as "the polymer"). Owing to use of such a polymer, the decomposition reaction and crosslinking reaction of a hydrophilic polymer due to irradiation sterilization treatment and during storage for a long term, or at high temperature are suppressed, with the result that a separation membrane for blood processing excellent in blood compatibility and in stability of membrane performance can be obtained. Also, the separation membrane for blood processing having a satisfactory air-bleeding during priming of the separation membrane for blood processing can be obtained.

<Polysulfone Polymer>

The polysulfone polymer refers to a sulfone ($-SO_2-$) group-containing synthetic polymer excellent in heat resistance and chemical resistance.

Examples of the polysulfone polymer include polysulfone, polyethersulfone, polyphenylenesulfone, polyarylethersulfone and a copolymer of these.

The polysulfone polymers may be used singly or as a mixture of two or more.

Among the polysulfone polymers, in view of controlling fractionation property, e.g., a polysulfone polymer represented by the following formula (1) or the following formula (2) is preferable.

$$(-Ar-SO_2-Ar-O-Ar-C(CH_3)_2-Ar-O-)_n \quad (1)$$

$$(-Ar-SO_2-Ar-O-)_n \quad (2)$$

In the formula (1) and formula (2), Ar represents a benzene ring; and n represents the number of repeat units in the polymer. The polysulfone represented by the formula (1) is commercially available under the name of, for example, "Udel™" from Solvay S. A. and "Ultrason™" from BASF SE. The polyethersulfone represented by the formula (2) is commercially available under the name of "Sumikaexcel™" from Sumitomo Chemical Co., Ltd. Since several types of products are present depending upon the degree of polymerization and the like, these can be appropriately used.

<Hydrophilic Polymer>

The hydrophilic polymer refers to a polymer having affinity for water, in particular, having blood compatibility.

Examples of the hydrophilic polymer include a (co)polymer containing vinylpyrrolidone or a (co)polymer containing an alkylene oxide. The (co)polymer containing vinylpyrrolidone as the hydrophilic polymer refers to a (co)polymer obtained by using vinylpyrrolidone as a monomer.

The hydrophilic polymers may be used singly or as a mixture of two or more.

Owing to use of a hydrophilic polymer as a membrane base material, a separation membrane realizing fractionation control depending upon the use and having a micro membrane structure described later can be obtained.

Among the hydrophilic polymers, in view of high blood compatibility, a polyvinylpyrrolidone is preferable. The polyvinylpyrrolidone refers to a water soluble polymer compound obtained by vinyl-polymerization of N-vinylpyrrolidone and widely used in a base material for a hollow-fiber membrane, as a hydrophilizing agent and a hole-forming agent. Polyvinylpyrrolidone is commercially available under the name of "LUVITEC™" from BASF SE. Since several types of polyvinylpyrrolidones different in molecular weight are available, these can be appropriately used.

<Polymer Having Hydroxy Group in Side Chain and Having Solubility of 0.5 g or Less in Water (100 g) at 20° C.>

The separation membrane of the embodiment contains a polymer having a hydroxy group in a side chain and having a solubility of 0.5 g or less in water (100 g) at 20° C., as a membrane base material.

Owing to containing a polymer having a hydroxy group in a side chain and having a solubility of 0.5 g or less in water (100 g) at 20° C. in addition to a polysulfone polymer and a hydrophilic polymer, as a membrane base material for the separation membrane, the separation membrane having blood compatibility, storage stability and satisfactory air-bleeding during priming can be obtained.

Herein, the polymer having a hydroxy group in a side chain refers to a polymer obtained by polymerizing only a monomer having a hydroxy group in a side chain or polymerizing so as to partly contain such a monomer. The latter polymer having a hydroxy group in a side chain can be obtained by copolymerizing a monomer having a hydroxy group in a side chain and a monomer having no hydroxy group in a side chain.

The side chain is a term used in contrast to a main chain, which is a portion composed by binding repeat units.

Examples of the side chain having a hydroxy group that the monomer has include an alkyl group having a hydroxy group such as a hydroxyethyl group, a hydroxypropyl group and a hydroxybutyl group; and an aromatic group having a hydroxy group. Examples of the monomer having a hydroxy group in a side chain include an acrylate monomer and methacrylate monomer having a hydroxy group in a side chain.

Specific examples of such monomers include hydroxyethyl acrylate, hydroxypropyl acrylate, hydroxybutyl acrylate, hydroxyethyl methacrylate, hydroxypropyl methacrylate and hydroxybutyl methacrylate.

Examples of the polymer having a hydroxy group in a side chain include polyvinyl alcohol, poly(hydroxyethyl acrylate), poly(hydroxypropyl acrylate), poly(hydroxybutyl acrylate), poly(hydroxyethyl methacrylate), poly(hydroxypropyl methacrylate) and poly(hydroxybutyl methacrylate). In the embodiment, polyvinyl alcohol, which is exemplified as the polymer having a hydroxy group in a side chain, is not actually produced from vinyl alcohol; however, since vinyl alcohol can be considered as a virtual monomer of polyvinyl alcohol, the polyvinyl alcohol is regarded as the polymer having a hydroxy group in a side chain.

In the embodiment, the polymer having a hydroxy group in a side chain and having a solubility of 0.5 g or less in water (100 g) at 20° C. is required to be insoluble or hard to soluble in water in order to prevent elution into a treatment liquid. Thus, as the polymers having a hydroxy group in a side chain, a polymer having a solubility of 0.5 g or less in water (100 g) at 20° C. is used. The solubility in water (100 g) of the polymer having a hydroxy group in a side chain is more preferably less than 0.1 g.

The solubility of the polymer can be obtained from (1) the polymer itself and (2) the polymer present in a separation membrane.

(1) The solubility can be obtained by use of the polymer as follows. Water (100 g) and a rotator are placed in a flask. The temperature of the flask is controlled to be 20° C. in a thermostat bath. In the flask, the polymer (5 g) to be measured is charged. The mixture is stirred for 12 hours or more, filtered by use of a filter (No. 5A) and dried at 60° C. until the whole filter reaches a constant amount. Then, the weight of insoluble matter is weighed. The difference between the amount charged (5 g) and the weight of the insoluble matter is regarded as the solubility in water (100 g).

(2) The solubility of a polymer can be obtained from the separation membrane as follows. A blood processing apparatus is broken down to obtain a separation membrane. The obtained separation membrane is dissolved in dimethylformamide so as to obtain a concentration of 50 mass %. The dimethylformamide solution in which the separation membrane is dissolved is gently poured in pure water of 20° C. having a weight 100 fold as high as the weight of the dimethylformamide solution dissolving the separation membrane. The resultant solution is centrifuged (5000 g or more, 20° C., 15 minutes) to separate the solution into a precipitated solid content (A) mainly containing a polysulfone polymer and an aqueous solution (B). The aqueous solution (B) is removed to leave the solid content (A) alone in the centrifuge tube. To the centrifuge tube having the solid content (A) remained therein, fresh pure water (about a half weight of the aqueous solution (B)) is added. The mixture is stirred at 80° C. for one hour. After completion of stirring, the mixture is cooled to 20° C. or less and centrifuged (5000 g or more, 20° C., 15 minutes) to separate a solid content from pure water portion, which is then discarded. This operation is repeated three times. The resultant solid content (A) was dried and weighed. The obtained solid content (A) is soaked in ethanol having a weight 10 fold as high as the weight of the solid content. The solution mixture is stirred at 20° C. for 12 hours or more in a thermostat bath. After stirring, ethanol containing a solid content is filtered. At this time, the polysulfone polymer is not dissolved in ethanol and the polymer and an oligomer component of a polysulfone polymer are extracted. The component of the polymer is fractionated by gel filtration chromatography, etc. Fractionation is simply performed by using ethanol as an eluent. The fractionated polymer is dried by evaporating ethanol. The solubility of the polymer obtained is obtained as described in the above (1). When the polymer is present in the above aqueous solution (B), the solid content is obtained by vaporizing the aqueous solution. The solid content is dissolved again in pure water of 20° C. having a weight 100 fold as high as the weight of the solid content. At this time, if the solid content is completely dissolved, the solubility of the polymer is determined as high as more than 0.5 g. If residue remains, the residue is collected by filtration and dried, and thereafter the solubility is obtained as described in the above (1).

In the embodiment, although the solubility of the polymer is preferably obtained in accordance with (1), the solubility may be obtained in accordance with (2). In the embodiment, if the solubility obtained in accordance with (2) is 0.5 g or less, the solubility of the polymer in water (100 g) at 20° C. can be determined as 0.5 g or less.

In the embodiment, the higher the molecular weight the polymer has, the lower the amount of elution from the separation membrane is. Therefore, the polymer to be used has a weight average molecular weight of preferably 200,000 or more and more preferably 300,000 or more. Furthermore, in view of controlling solubility of the polymer having a hydroxy group in a side chain in water (100 g) to fall within a desired range, the weight average molecular weight of the polymer having a hydroxy group in a side chain is preferably 200,000 or more.

In the embodiment, as the polymer to be used, a single polymer or a mixture of two or more polymers may be used.

In the embodiment, in order to improve the protection effect of a hydrophilic polymer of the separation membrane, the polymer to be used is desirably added in a larger amount in the separation membrane; however, in view of preventing elution, the polymer is better to add in a smaller amount. Therefore, it is necessary to appropriately consider the amount of polymer to be added (content) in consideration of balance between them.

The content [A] of the polymer in the separation membrane is preferably 0.01 to 0.6 mass % and more preferably 0.02 to 0.5 mass % in the solid content of separation membrane base material, in view of protection effect of a hydrophilic polymer and prevention of elution.

The reason why the separation membrane of the embodiment acquires satisfactory blood compatibility and excellent storage stability by adding the polymer to the separation membrane is presumably because radicals generated due to oxygen, temperature, i.e., heat, and light, etc. during storage can be removed by hydroxy groups. Furthermore, the reason why the separation membrane of the embodiment maintains biocompatibility even if irradiation sterilization is applied by adding the polymer to the separation membrane is presumably because radicals produced during irradiation sterilization can be removed by hydroxy groups. When radicals generated by heat, light and oxygen, etc. during sterilization treatment or storage of the separation membrane cannot be removed, the decomposition reaction or crosslinking reaction of a polysulfone polymer and a hydrophilic polymer constituting a base material for the separation membrane proceeds. The polysulfone polymer is relatively resistant against the decomposition reaction and crosslinking reaction; however, the decomposition reaction and crosslinking reaction of the hydrophilic polymer such as a polyvinylpyrrolidone easily proceed. If the decomposition reaction and crosslinking reaction of the hydrophilic polymer proceed, the content ratio of the polysulfone polymer increases in the surface of the separation membrane. As a result, adsorption of proteins and adhesion of blood cell components proceed during blood processing and blood compatibility significantly reduces. In addition, elution of a membrane base material, particularly, a decomposition product derived from a hydrophilic polymer, into a treatment liquid, i.e. blood, is highly concerned.

In the separation membrane of the embodiment, as described above, it is considered that a membrane base material, particularly, a hydrophilic polymer, can be protected from radicals produced during sterilization or storage, by adding the polymer.

In the embodiment, the polymer to be used is preferably allowed to localize in the functional separation surface of the separation membrane. If the polymer is added to the entire separation membrane, the protection effect from radicals can be exerted by the entire membrane; however, the polymer having extremely low solubility is added to portions other than the functional separation surface. As a result, wettability decreases and air-bleeding is not sufficiently performed during priming. If the air-bleeding is not sufficiently performed, it becomes difficult to exchange solution in membrane holes, with the result that the amount of priming solution increases and economic efficiency decreases. Besides this, air leakage occurs during blood processing and false detection may occur. Thus, adding the polymer to the entire separation membrane is not preferable. In the embodiment, it is possible to maintain the state where a hydrophilic polymer is exposed in the surface of a porous structure present inside the membrane by localizing the polymer in the functional separation surface of the separation membrane. In addition, the air-bleeding of an interior portion of hollow-fiber membrane during priming is significantly improved. Maintaining blood compatibility etc., for a long term is a requisite property of the functional separation surface. Thus, the polymer may be added to the functional separation surface. In view of serving and maintaining membrane function in a separator, the average concentration of the polymer in the functional separation surface is 20 mass % or more and preferably 30 mass % or more.

Herein, the average concentration [B] of the polymer in the functional separation surface refers to an average value of polymer concentrations measured at several points (3 or more) in the functional separation surface of the separation membrane.

In the blood processing apparatus, the smaller the variation of the concentration of the polymer in the functional separation surface of the separation membrane, the more stable the entire blood processing apparatus. The maximum values and minimum values of the polymer concentrations measured at several points fall within the range of the average concentration obtained from the results of several points±15%, and preferably within the range of the average concentration±10%. The phrase that the maximum value and minimum value fall within the range of the average concentration±15% means that both the maximum value and minimum value fall within the range from (the average concentration of the polymer−15) % to (the average concentration of the polymer+15) %.

To prevent priming performance from decreasing, it is desired that the polymer of the separation membrane is localized in the functional separation surface. The average concentration [B] of the polymer in the functional separation surface is divided by the content [A] of the polymer in the separation membrane, i.e., the ratio ([B]/[A]) of the average concentration of the polymer in the functional separation surface to the content of the polymer in the separation membrane is 100 fold or more and preferably 130 fold or more.

In the embodiment, the functional separation surface refers to the surface of the separation membrane on which separation function is executed. A blood processing apparatus has a separation membrane by which a part to which a liquid to be separated is introduced is isolated from a part from which a liquid permeated through the separation membrane is discharged. When the separation membrane is a sheet, the surface of the separation membrane facing the part to which the liquid to be separated is introduced is a functional separation surface. When the separation membrane is a hollow fiber, more specifically, when the liquid to be separated is supplied in a hollow-fiber membrane and permeates toward the outside, the inner surface of the hollow-fiber membrane is a functional separation surface. Conversely, when the liquid to be separated permeates from the outside the hollow-fiber membrane toward the inside, the outer surface of the hollow-fiber membrane is the functional separation surface.

As a method for analyzing the polymer composition constituting a functional separation surface, for example, X-ray Photoelectron spectroscopy (XPS and ESCA (Electron Spectroscopy for Chemical Analysis)) is suitable. Since information of the polymer composition on the top surface can be obtained, only the composition of the surface executing a separation function can be accurately detected by XPS.

Note that the "surface" of the functional separation surface defined in the present invention is not limited to a contact surface (two-dimensional plane) and conceptionally includes the portion present at a certain depth from the surface of the membrane. For example, even if the surface analysis method such as XPS as mentioned above is used, the region to be analyzed is not limited to a contact surface (two-dimensional plane) in a strict sense and a two-dimensional plane including the portion present at a certain depth is analyzed and evaluated. Note that the depth in the thickness direction of the membrane detectable by XPS is expressed by a value in the order of nm. Such a surface analysis method is appropriate as a measurement method for the concentration of the polymer in the functional separation surface.

In the embodiment, the concentration of the polymer in a functional separation surface and the content of the polymer in a separation membrane can be measured by the method specifically described in Examples.

In the embodiment, as a method for adding the polymer to a separation membrane, a method of blending and dissolving the polymer in a coagulation liquid is preferably used. A method of molding a membrane by blending and dissolving the polymer in a spinning dope is not preferable since the polymer is added to the entire separation membrane, with the result that air-bleeding is not sufficiently performed as described above. After a separation membrane is obtained, a blood processing apparatus is assembled and then the solution dissolving the polymer is supplied to apply the polymer onto the functional separation surface. This is another method. Since the polymer is hard to soluble in water, usually the polymer is dissolved in an organic solvent, in which a polysulfone polymer is not dissolved, and then applied. At this time, an alcohol or an aqueous alcohol solution, etc. is suitable as an organic solvent; however since an alcohol swells a polysulfone polymer, penetration of the polymer in the thickness direction of the membrane is observed. When the less soluble polymer penetrated attaches to membrane holes, wettability reduces. As a result, air-bleeding is not sufficiently performed during priming and liquid in membrane holes is not easily exchanged. For this reason, an alcohol is not preferred. Also in the coating method, it is difficult to add the polymer uniformly to the functional separation surface of the separation membrane in a blood processing apparatus. In other words, the amount to be added varies between the sites, e.g., between the upper portion and lower portion of a blood processing apparatus and between the inner and outer circumferences, functional separation surfaces different in stability are provided within the same treatment apparatus. In this respect, the coating method is not preferred.

For the reasons described above, a method of blending and dissolving the polymer in a coagulation liquid for forming a membrane is preferred. Furthermore, in this method, while the amount of polymer to be used is suppressed, the polymer can be localized in the functional separation surface of the separation membrane. For example, if a bore liquid dissolving the polymer used as a coagulation liquid and a spinning dope containing a polysulfone polymer, a hydrophilic polymer and a solvent, are also ejected from a tube-in-orifice type spinneret, the polymer and the hydrophilic polymer can be present together.

<Blood Processing Apparatus>

The blood processing apparatus of the embodiment, in which the separation membrane of the embodiment is installed, is used as a hemodialyzer, a hemofilter, a blood fractionor, a blood plasma separator etc., for use in an extracorporeal-circulation blood purification therapy.

When blood is treated by the separation membrane installed in a blood processing apparatus, satisfactory blood compatibility and storage stability are obtained, and even if irradiation sterilization treatment is applied, membrane performance does not decrease.

The blood processing apparatus is preferably used in a hemodialyzer, a hemofilter and a hemodialysis filter, etc., and more preferably used in sustainable applications of these such as a continuous hemodialyzer, a continuous hemofilter and a continuous hemodialysis filter. The detail specifications of the separation membrane such as dimension and fractionation are determined depending upon the uses.

The shape of the separation membrane to be installed in a blood processing apparatus is preferably a hollow fiber shape.

<Method for Manufacturing Blood Processing Apparatus>

Now, a method for manufacturing the blood processing apparatus of the embodiment, in which a hollow-fiber membrane is used as the separation membrane, a polysulfone as a polysulfone polymer, and a polyvinylpyrrolidone as a hydrophilic polymer, will be described below as an example.

A spinning dope for forming a hollow fiber can be prepared by dissolving a polysulfone and a polyvinylpyrrolidone in a solvent. Examples of the solvent include dimethylacetamide, dimethylsulfoxide, N-methyl-2-pyrrolidone, dimethylformamide (DMF), sulfolane and dioxane.

These solvents may be used singly or as a solvent mixture of two or more. Furthermore, it is preferable that additives are not added to a spinning dope as much as possible since the additives tend to damage stability of the spinning dope; however additives such as water may be added.

The concentration of the polysulfone in the spinning dope is not particularly limited as long as a membrane can be formed and the obtained separation membrane can serve as a permeation membrane. More specifically, the concentration of polysulfone is preferably 5 to 35 mass % and more preferably 10 to 30 mass %. To attain high water permeability, the concentration of polysulfone is preferably low and further preferably 10 to 25 mass %.

The concentration of the polyvinylpyrrolidone in the spinning dope is controlled in such a way that the blending ratio of the polyvinylpyrrolidone to the polysulfone becomes preferably 27 mass % or less, more preferably 18 to 27 mass % and further preferably 20 to 27 mass %.

If the blending ratio of the polyvinylpyrrolidone to the polysulfone is controlled to be 27 mass % or less, the amount of polyvinylpyrrolidone to be eluted can be suppressed. Furthermore, if the blending ratio is controlled to be a preferable value of 18 mass % or more, the concentration of the polyvinylpyrrolidone in the functional separation surface can be controlled to fall within a preferable range, with the result that the effect of suppressing protein adsorption can be increased and excellent blood compatibility can be obtained.

Subsequently, a spinning dope is ejected by use of tube-in-orifice type spinneret from the orifice of the spinneret also with a bore liquid for coagulating the spinning dope in air from the tube. As the bore liquid, water or a coagulation liquid mainly containing water can be used. Generally, a solution mixture of the same solvent as used in a spinning dope and water is preferably used. For example, a 20 to 70 mass % aqueous dimethylacetamide solution is used. As the ratio of solvent employed in the spinning dope in the bore liquid increases, penetration of the polymer dissolved therein in the thickness direction of the membrane is observed. When the less soluble polymer penetrated is attached to membrane holes, wettability decreases, and air-bleeding is not sufficiently performed during priming. As a result, it becomes difficult to exchange a liquid in the membrane holes and priming performance decreases. In contrast, if the concentration of the polymer is extremely low, the concentration of the polymer in the functional separation surface cannot reach 20 mass % or more. The polymer is dissolved in a desirable concentration in the bore liquid. The concentration of the preferably falls within the range of 0.005 mass % to 1 mass % of the bore liquid and more preferably within the range of 0.01 mass % to 0.1 mass %.

At this time, if an amount of spinning dope to be ejected and an amount of bore liquid to be ejected are controlled, the inner diameter and the thickness of the hollow-fiber membrane can be obtained in desired values.

The inner diameter of the hollow-fiber membrane is satisfactorily 170 to 250 μm for blood processing and more preferably 180 to 220 μm. In view of efficiency of diffusion removal of low molecular weight substances by the mass transfer resistance of a permeation membrane, the thickness of hollow-fiber membrane is preferably 50 μm or less.

The spinning dope ejected from a spinneret together with a bore liquid, flows through an air gap portion and is introduced in a coagulation bath mainly containing water and arranged under the spinneret. The spinning dope is soaked therein for a predetermined time to complete coagulation. At this time, in view of effective air-bleeding during priming, a draft, which is expressed by the ratio of a spinning dope ejection linear velocity and a take-over speed, is preferably 1 or less.

The air gap refers to the space between a spinneret and a coagulation bath. The spinning dope is started to coagulate from the inner surface by a poor solvent component such as water in a bore liquid simultaneously ejected from the spinneret.

If the draft is larger than 1, the phase separation, which is a phenomenon starting when the ejected spinning dope comes into contact with the bore liquid and coagulates, changes, and the polymer dissolved in the bore liquid penetrates in the thickness direction of the membrane. If the less soluble polymer penetrated is attached to membrane holes, wettability decreases and air-bleeding is not sufficiently performed during priming. As a result, it becomes difficult to exchange a liquid in the membrane holes (decrease of priming performance). To prevent penetration of the polymer dissolved in a bore liquid in the thickness direction of the membrane at the coagulation initiation time and to form a smooth surface of the separation membrane, thereby stabilizing the separation membrane structure, the draft is preferably 1 or less and more preferably 0.95 or less.

Subsequently, the hollow-fiber membrane, after the solvent remaining thereon is removed by washing with hot water, etc., is continuously introduced in a dryer and dried with hot air, etc. to obtain the dry hollow-fiber membrane.

Washing is made in order to remove unnecessary hydrophilic polymers, preferably with hot water of 60° C. or more for 120 seconds or more and more preferably with hot water of 70° C. or more for 150 seconds or more.

The hollow-fiber membrane, since it is embedded with a urethane resin in the later step, is preferably dried such that the hollow-fiber membrane has a water content of 100% or less relative to the dry weight of the hollow-fiber membrane and more preferably 20% or less.

The hollow-fiber membrane pieces obtained through the aforementioned steps, are sheaved into a bundle the number and length of which have been determined so as to satisfy a desired membrane area, and subjected to a module manufacturing step. In this step, the hollow-fiber membrane bundle is charged in a cylindrical container having two nozzles near both ends of the side surface and the both ends are embedded with a urethane resin. Subsequently, hardened urethane portion is cut to obtain a hollow-fiber membrane having open ends. To the open ends, a header cap having a nozzle for introducing (ejecting) a liquid is provided. In this manner, a blood processing apparatus is assembled. Subsequently, irradiation sterilization treatment is applied to the blood processing apparatus having the hollow-fiber separation membrane installed therein. In the method of irradiation sterilization, any one of an electron beam, gamma beam and X ray, etc. can be used. The radiation dose of electron beam or gamma beam falls usually within the range of 5 to 50 kGy and preferably 20 to 40 kGy. If irradiation sterilization is applied under such conditions, a polyvinylpyrrolidone constituting a hollow-fiber membrane is partially crosslinked. In this manner, elution of polyvinylpyrrolidone can be suppressed while maintaining satisfactory blood compatibility. Through the sterilization step such as the irradiation sterilization, manufacturing of a blood processing apparatus is completed.

EXAMPLES

The present invention will be more specifically described by way of Examples and Comparative Examples; however, the present invention is not limited to these Examples. Note that measurement methods employed in Examples are as follows.

[Measurement of Solubility]

Water (100 g) and a rotator were placed in a flask. The temperature of the flask was controlled to be 20° C. in a thermostat bath. The polymer (5 g) to be measured was charged in the flask and stirred for 12 hours or more. The resultant mixture was filtered by use of a filter (No. 5A) and dried at 60° C. until the whole filter reached a constant amount. Then, the weight of insoluble matter was weighed. The difference between the amount charged (5 g) and the weight of the insoluble matter was regarded as the solubility in water (100 g). If insoluble matter was not filtered out, the solubility was determined as 5 g or more; whereas if the difference between the amount charged (5 g) and the weight of insoluble matter was less than 0.1 g, the solubility was determined as less than 0.1 g, which means almost insoluble.

[Measurement of Weight Average Molecular Weight]

With the polymer to be measured, an eluent was blended to prepare a solution having a polymer concentration of 1.0 mg/mL. The solution was allowed to stand still overnight to dissolve the polymer and filtered by a 0.45-micron filter. The obtained filtrate was used as a sample. The weight average molecular weight of the polymer was determined by use of gel permeation chromatography in the following conditions.

Data processing: Tosoh GPC-8020
    Apparatus: Tosoh HLC-8220GPC
    Column: Two columns of TSK gel Super AWM-H (6.0 mm ID×15 cm)
    Oven: 40° C.
    Eluent: 5 mmol/L LiBr in DMF (0.6 mL/min)
    Amount of sample: 40 μL×1.0 mg/mL
    Detector: RI
    Calibration curve: Polystyrene (EasiCal (PS-1) manufactured by Agilent Technologies, Inc.)

[Measurement of Content of Polymer in Separation Membrane]

A blood processing apparatus was broken down to obtain a separation membrane. From the obtained separation membrane, 30 mg from the membrane pieces was dissolved in deuterated dimethylformamide so as to obtain a concentration of 5 mass %. The dissolution solution of the separation membrane was measured by a nuclear magnetic resonance apparatus in the following conditions to quantitatively determine the content of the polymer in the separation membrane.

Measurement apparatus: Bruker Biospin Avance 600
    Nucleus to be observed: $^1$H
    Observation frequency: 600 MHz
    Cumulated number: 1024 times A peak derived from a phenyl proton present at the ortho position of an ether bond in the vicinity of 7 ppm was used as a polysulfone peak; a peak derived from $CH_2$ adjacent to N in the vicinity of 3.3 ppm as a polyvinylpyrrolidone peak; and a peak derived from an OH group in the vicinity of 5 ppm as a poly(hydroxypropyl methacrylate) peak to obtain integral intensities. From these, the contents in individual polymer components were obtained.

[Measurement of Concentration of Polymer in Functional Separation Surface]

A separation membrane was taken from a blood processing apparatus. When the blood processing apparatus was a hollow-fiber membrane module, one was taken from the center of a bundle of hollow-fiber membrane pieces, one from a portion of the outer circumference of the bundle and one from the opposite portion of the outer circumference. In total, three hollow-fiber membrane pieces were sampled. Measurement was performed at three points, i.e., center, and midpoints of the center and both ends of a single hollow-fiber membrane piece sampled in the fiber axis direction. In total, 9 points were measured. In each point, the separation membrane was cut along the fiber axis to expose the functional separation surface. The concentration of the polymer in the functional separation surface was measured by X-ray photoelectron spectroscopy in the following conditions. In the case where a wet membrane or a protecting agent was added, a hollow-fiber membrane was washed with pure water and lyophilized and then measurement was performed.

Measurement apparatus: Thermo Fisher ESCALAB250
    Excitation source: Monochromatic $AlK_\alpha$ 15 kV×10 mA
    Analysis size: About 1 mm
    Photoelectron escape angle: 0° (the axis of beam splitter is perpendicular to the surface of a sample)
    Pulse energy: 20 eV The concentration of the polymer in a functional separation surface was determined based on the ester group present in an acrylate polymer and a methacrylate polymer in accordance with the following procedure. The amounts of carbon, oxygen, nitrogen and sulfur were obtained respectively based on integrated intensities of C1s, O1s, N1s and S2p by use of relative sensitivity coefficients of elements (C1s: 1.00, O1s: 2.72, N1s: 1.68, S2p: 1.98), as relative amounts (atomic %).

Quantification of an ester group was performed by peak splitting of C1s, more specifically, by calculating the ratio of the peak area derived from an ester group relative to all elements (except hydrogen). This was determined as the amount of carbon derived from an ester group (atomic %). At this time, peak splitting of C1s was performed by five components: a component derived from C—H, C—C, C=C and C—S bonds; a component derived from C—O and C—N bonds; a component derived from C=O (amide bond); a component derived from an ester group and a π-π* shake up component. Furthermore, the amount of sulfur (atomic %) was used as an index of a polysulfone and the amount of nitrogen (atomic %) was used as an index of polyvinylpyrrolidone. When poly(hydroxypropyl methacrylate) was used as the polymer, the molecular weight of monomer was 144 and the concentration of the polymer in the functional separation surface was calculated from the following expression:

Concentration of polymer(mass %) in functional separation surface=("amount of carbon derived from an ester group"×144/("amount of nitrogen"×111+amount of sulfur×442+"amount of carbon derived from an ester group"×144))×100

Where 111 is the molecular weight of polyvinylpyrrolidone monomer and 442 is the molecular weight of polysulfone monomer. The average value of the concentrations of the polymer at nine points in total was regarded as the average concentration of the polymer in the functional separation surface and a maximum value and a minimum value of the concentrations at the nine points were compared to the average concentration.

When a polymer other than an acrylate polymer and a methacrylate polymer is used, calculation may be made from the peaks other than an ester group.

[Ratio of Average Concentration of Polymer in Functional Separation Surface to Content of Polymer in Separation Membrane]

The ratio of the average concentration of the polymer in a functional separation surface to the content of the polymer in a separation membrane was calculated from the aforementioned evaluation results in accordance with the following expression.

> Ratio of average concentration of polymer in functional separation surface to content of polymer in separation membrane=concentration of polymer(mass %) in functional separation surface/content of polymer(mass %) in separation membrane

[Evaluation of Air-Bleeding During Priming]

The case where a blood processing apparatus is a hollow fiber membrane-based module will be described. Lines were connected to each of a blood part and a dialyzed-fluid part. A port of the dialyzed-fluid part was plugged and an inlet port of the blood part was allowed to face down. In this state, physiological saline (Otsuka Normal Saline, manufactured by Otsuka Pharmaceutical Co., Ltd.) was supplied from the inlet port of the blood part at a rate of 100 mL/minute for 3 minutes, and the lines of the inlet port and outlet port of the blood part were stopped by use of forcipes. Subsequently, physiological saline was supplied from the port of a dialyzed-fluid part upward from the bottom at a rate of 500 mL/minute for one minute, and then, the lines of the inlet port and outlet port of the dialyzed-fluid part were stopped by use of forcipes. In this way, the blood processing apparatus was completely filled with physiological saline. Forcipes of the inlet port of the blood part and the outlet port of the dialyzed-fluid part were removed to allow the physiological saline to flow from the inlet port of the blood part through a filter (membrane) at a rate of 100 mL/minute. At this time, air bubbles in the physiological saline flowing toward the outlet port of the dialyzed-fluid part through the membrane were visually observed.

The case where air bubbles disappear within one minute was evaluated as satisfactory and expressed by reference symbol "○"; the case where air bubbles disappear within 3 minutes beyond one minute was expressed by reference symbol "Δ"; and the case where 5 minutes or more was required until air bubbles disappear was evaluated as unsatisfactory and expressed by reference symbol "x."

[Measurement of Lactate Dehydrogenase (LDH) Activity]

The blood compatibility of a separation membrane was evaluated based on adherability of platelets to a membrane surface and quantified based on the activity of lactate dehydrogenase contained in the platelets attached to the separation membrane.

A blood processing apparatus was washed with physiological saline (Otsuka Normal Saline, manufactured by Otsuka Pharmaceutical Co., Ltd.). After priming, the blood processing apparatus was broken down and the separation membrane was taken out. The both ends of the separation membrane were processed with silicon such that an effective length was 15 cm and the area of an inner surface of the membrane was $5 \times 10^{-3}$ m$^2$ to fabricate a mini module.

To the mini module, physiological saline (10 mL) was supplied to wash the insides of hollow fibers. Thereafter, human blood to which heparin was added (15 mL (heparin 1000 IU/L)), was circulated at a flow rate of 1.3 mL/min through the mini module prepared above at 37° C. for 4 hours. The inside and outside of the mini module were washed separately with physiological saline (10 mL). From the mini module thus washed, a half of all hollow-fiber membrane pieces of 7 cm in length were taken, cut into pieces, placed in a spitz type tube for LDH measurement and used as a measurement sample.

Then, a 0.5 vol % Triton X-100/PBS solution (0.5 mL), which was obtained by dissolving Triton X-100 (manufactured by Nacalai Tesque, Inc.) in phosphate buffer (PBS) (manufactured by Wako Pure Chemical Industries, Ltd.), was added to the LDH measurement spitz pipe and treated with ultrasonic wave for 60 minutes to break the cells (primarily, platelets) attached to the hollow-fiber membrane. In this way, LDH in the cells was extracted. An aliquot (0.05 mL) was taken from the extract. To the aliquot, a 0.6 mM sodium pyruvate solution (2.7 mL) and a 1.277 mg/mL nicotinamide adenine dinucleotide (NADH) solution (0.3 mL) were added to react them. Immediately after the reaction, an aliquot (0.5 mL) was taken and the absorbance thereof was measured at 340 nm. The remaining liquid was further reacted at 37° C. for one hour and thereafter the absorbance thereof was measured at 340 nm. A reduction in absorbance from immediately after the reaction was determined. Absorbance of the membrane (blank), which was not reacted with blood, was measured in the same manner. The difference in absorbance was calculated in accordance with the following expression. In this method, the larger the reduction is, the higher the LDH activity is, more specifically, the larger the amount of platelets adhered to a membrane surface. Measurement was performed three times and an average value thereof was described as the difference in absorbance.

> Δ340 nm=(absorbance of sample immediately after reaction–absorbance of sample after 60 minutes)–(absorbance of blank immediately after reaction–absorbance of blank after 60 minutes)

[Measurement of Amount of Elution]

The eluted substances after a blood processing apparatus was fabricated (t=0) and the eluted substances from the apparatus stored at 60° C. for one month were compared based on UV and used as an index of storage stability.

Based on the dialysis-based artificial kidney apparatus manufacturing approval standard, measurement was performed. From the blood processing apparatus, the separation membrane (1 g) was taken, soaked in pure water (100 mL) and extracted at 70° C. for one hour. The extract was used as a test liquid. Absorbance of the test liquid was measured at 220 to 350 nm by a spectrophotometer for ultraviolet and visible region.

Example 1

As the polymer, poly(hydroxypropyl methacrylate) (PHPMA, manufactured by Aldrich Chemical Co.) was used. The solubility of the polymer in water (100 g) was less than 0.1 g and the weight average molecular weight thereof was 330,000.

A polysulfone (PS) (P-1700, manufactured by Solvay S.A.) (17 parts by mass), a polyvinylpyrrolidone (PVP) (K-90, manufactured by BASF SE) (4 parts by mass) and dimethylacetamide (special-grade reagent, manufactured by Kishida Chemical Co., Ltd.) (79 parts by mass) were blended to prepare a spinning dope.

A bore liquid was prepared by dissolving poly(hydroxypropyl methacrylate) in a 60 mass % aqueous dimethylacetamide solution so as to have a concentration of 0.03 mass %.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.91. After washing with water and drying, a hollow separation membrane was obtained.

Herein, water-washing was performed at a temperature of 90° C. for 180 seconds. The amounts of spinning dope and bore liquid ejected were controlled such that the thickness the membrane after dry became 35 μm and the inner diameter became 185 μm.

From the obtained separation membrane, a module having an effective membrane area of 1.5 m² was assembled and sterilized by application of an electron beam to obtain a blood processing apparatus.

Air bubbles disappeared within one minute. Thus, air-bleeding was satisfactory.

The content of the polymer in the separation membrane was 0.19 mass %, the average concentration of the polymer in the functional separation surface was 34 mass %. A maximum concentration value of the polymer in the functional separation surface was 41 mass % and the minimum value thereof was 30 mass %. The maximum value and minimum value fell within the range of an average concentration±15%. The variation was small. The ratio of the average concentration of the polymer in the functional separation surface and the content of the polymer in the separation membrane was 179.

The LDH activity was as good as 14 [Δabs/hr/m²].

The amount of elution was evaluated. As a result, the absorbance after the treatment apparatus was prepared was 0.041 and the absorbance after storage at 60° C. for one month was 0.044, which satisfied a standard value of 0.1 or less.

Example 2

As the polymer, poly(hydroxyethyl methacrylate) (PHEMA, manufactured by Aldrich Chemical Co.) was used. The solubility of the polymer in water (100 g) was less than 0.1 g and the weight average molecular weight thereof was 1,700,000.

The spinning dope described in Example 1 was used.

A bore liquid was prepared by dissolving poly(hydroxyethyl methacrylate) in a 60 mass % aqueous dimethylacetamide solution so as to have a concentration of 0.01 mass %.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.91. After washing with water and drying, a hollow separation membrane was obtained. Herein, water-washing was performed at a temperature of 90° C. for 180 seconds. The amounts of spinning dope and bore liquid ejected were controlled such that the thickness of the membrane after dry became 35 μm and the inner diameter became 185 μm.

From the obtained separation membrane, a module having an effective membrane area of 1.5 m² was assembled and sterilized by application of an electron beam to obtain a blood processing apparatus.

Air bubbles disappeared within one minute. Thus, air-bleeding was satisfactory.

The content of the polymer in the separation membrane was 0.11 mass %, and the average concentration of the polymer in the functional separation surface was 21 mass %. A maximum concentration value of the polymer in the functional separation surface was 22 mass % and the minimum value thereof was 20 mass %. The maximum value and minimum value fell within the range of an average concentration±15%. The variation was small. The ratio of the average concentration of the polymer in the functional separation surface and the content of the polymer in the separation membrane was 191.

The LDH activity was as good as 12 [Δabs/hr/m²].

The amount of elution was evaluated. As a result, the absorbance after the treatment apparatus was prepared was 0.035 and the absorbance after storage at 60° C. for one month was 0.041, which satisfied a standard value of 0.1 or less.

Example 3

The polymer described in Example 2 was used.

The spinning dope described in Example 1 was used.

A bore liquid was prepared by dissolving poly(hydroxyethyl methacrylate) in a 60 mass % aqueous dimethylacetamide solution so as to have a concentration of 0.1 mass %.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.91. After washed with water and dried, a hollow separation membrane was obtained. Herein, water-washing was performed at a temperature of 90° C. for 180 seconds. The amounts of spinning dope and bore liquid ejected were controlled such that the thickness of the membrane after dry became 35 μm and the inner diameter became 185 μm.

From the obtained separation membrane, a module having an effective membrane area of 1.5 m² was assembled.

Air bubbles disappeared within one minute. Thus, air-bleeding was satisfactory.

The content of the polymer in the separation membrane was 0.60 mass %, and the average concentration of the polymer in the functional separation surface was 83 mass %. A maximum concentration value of the polymer in the functional separation surface was 90 mass % and the minimum value thereof was 79 mass %. The maximum value and minimum value fell within the range of an average concentration±15%. The variation was small. The ratio of the average concentration of the polymer in the functional separation surface and the content of the polymer in the separation membrane was 138.

The LDH activity was as good as 16 [Δabs/hr/m²].

The amount of elution was evaluated. As a result, the absorbance after the treatment apparatus was prepared was 0.032 and the absorbance after storage at 60° C. for one month was 0.040, which satisfied a standard value of 0.1 or less.

Example 4

The polymer described in Example 1 was used.

A polyethersulfone (PES) (Sumikaexcel 4800P manufactured by Sumitomo Chemical Co., Ltd.) (17 parts by mass), a polyvinylpyrrolidone (K-90, Manufactured by BASF SE) (4 parts by mass) and dimethylacetamide (special-grade reagent, manufactured by Kishida Chemical Co., Ltd.) (79 parts by mass) were blended to prepare a spinning dope.

A bore liquid was prepared by dissolving poly(hydroxypropyl methacrylate) in a 60 mass % aqueous dimethylacetamide solution so as to have a concentration of 0.03 mass %.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.98. After washed with water and dried, a hollow separation membrane was obtained. Herein, water-washing was performed at a temperature of 90° C. for 180 seconds. The amounts of spinning dope and bore liquid ejected were controlled such that the thickness of the membrane after dry became 35 µm and the inner diameter became 185 µm.

From the obtained separation membrane, a module having an effective membrane area of 1.5 m² was assembled and sterilized by application of an electron beam to obtain a blood processing apparatus.

Air bubbles disappeared within one minute. Thus, air-bleeding was satisfactory.

The content of the polymer in the separation membrane was 0.20 mass %, and the average concentration of the polymer in the functional separation surface was 36 mass %. A maximum concentration value of the polymer in the functional separation surface was 46 mass % and the minimum value thereof was 30 mass %. The maximum value and minimum value fell within the range of an average concentration±15%. The variation was small. The ratio of the average concentration of the polymer in the functional separation surface and the content of the polymer in the separation membrane was 180.

The LDH activity was as good as 19 [Δabs/hr/m²].

The amount of elution was evaluated. As a result, the absorbance after the treatment apparatus was prepared was 0.039 and the absorbance after storage at 60° C. for one month was 0.046, which satisfied a standard value of 0.1 or less.

Example 5

The polymer described in Example 1 was used.

A polysulfone (P-1700, manufactured by Solvay S.A.) (17 parts by mass), a poly(vinyl pyrrolidone-vinyl acetate) (VA64, Luvitec VA64 manufactured by BASF SE) (4 parts by mass) and dimethylacetamide (special-grade reagent, manufactured by Kishida Chemical Co., Ltd.) (79 parts by mass) were blended to prepare a spinning dope.

A bore liquid was prepared by dissolving poly(hydroxypropyl methacrylate) in a 60 mass % aqueous dimethylacetamide solution so as to have a concentration of 0.03 mass %.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.95. After washed with water and dried, a hollow separation membrane was obtained. Herein, water-washing was performed at a temperature of 90° C. for 180 seconds. The amounts of spinning dope and bore liquid ejected were controlled such that the thickness of the membrane after dry became 35 µm and the inner diameter became 185 µm.

From the obtained separation membrane, a module having an effective membrane area of 1.5 m² was assembled and sterilized by application of an electron beam to obtain a blood processing apparatus.

Air bubbles disappeared within one minute. Thus, air-bleeding was satisfactory.

The content of the polymer in the separation membrane was 0.16 mass %, and the average concentration of the polymer in the functional separation surface was 49 mass %. A maximum concentration value of the polymer in the functional separation surface was 57 mass % and the minimum value thereof was 43 mass %. The maximum value and minimum value fell within the range of an average concentration±15%. The variation was small. The ratio of the average concentration of the polymer in the functional separation surface and the content of the polymer in the separation membrane was 306.

The LDH activity was as good as 21 [Δabs/hr/m²].

The amount of elution was evaluated. As a result, the absorbance after the treatment apparatus was prepared was 0.034 and the absorbance after storage at 60° C. for one month was 0.039, which satisfied a standard value of 0.1 or less.

Example 6

As the polymer, a poly(hydroxyethyl methacrylate) (manufactured by Polymer Scientific Product) was used. The solubility of the polymer in water (100 g) was less than 0.1 g and the weight average molecular weight thereof was 200,000.

The spinning dope described in Example 1 was used.

A bore liquid was prepared by dissolving poly(hydroxyethyl methacrylate) in a 65 mass % aqueous dimethylacetamide solution so as to have a concentration of 0.05 mass %.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.95. After washed with water and dried, a hollow separation membrane was obtained. Herein, water-washing was performed at a temperature of 90° C. for 180 seconds. The amounts of spinning dope and bore liquid ejected were controlled such that the thickness of the membrane after dry became 35 µm and the inner diameter became 185 µm.

From the obtained separation membrane, a module having an effective membrane area of 1.5 m² was assembled and sterilized by gamma ray to obtain a blood processing apparatus.

Air bubbles disappeared within one minute. Thus, air-bleeding was satisfactory.

The content of the polymer in the separation membrane was 0.48 mass %, and the average concentration of the polymer in the functional separation surface was 48 mass %. A maximum concentration value of the polymer in the functional separation surface was 58 mass % and the minimum value thereof was 33 mass %. The maximum value and minimum value fell within the range of an average concentration±15%. The variation was small. The ratio of the average concentration of the polymer in the functional separation surface and the content of the polymer in the separation membrane was 100.

The LDH activity was as good as 18 [Δabs/hr/m²].

The amount of elution was evaluated. As a result, the absorbance after the treatment apparatus was prepared was 0.033 and the absorbance after storage at 60° C. for one month was 0.040, which satisfied a standard value of 0.1 or less.

Example 7

As the polymer, a poly(hydroxybutyl methacrylate) (PH-BMA, manufactured by Polymer Scientific Product) was used. The solubility of the polymer in water (100 g) was less than 0.1 g and the weight average molecular weight thereof was 380,000.

The spinning dope described in Example 1 was used.

A bore liquid was prepared by dissolving poly(hydroxybutyl methacrylate) in a 60 mass % aqueous dimethylacetamide solution so as to have a concentration of 0.03 mass %.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.91. After washed with water and dried, a hollow separation membrane was obtained. Herein, water-washing was performed at a temperature of 90° C. for 180 seconds. The amounts of spinning dope and bore liquid ejected were controlled such that the thickness of the membrane after dry became 35 µm and the inner diameter became 185 µm.

From the obtained separation membrane, a module having an effective membrane area of 1.5 m² was assembled and sterilized by application of a gamma beam to obtain a blood processing apparatus.

Air bubbles disappeared within one minute. Thus, air-bleeding was satisfactory.

The content of the polymer in the separation membrane was 0.18 mass %, and the average concentration of the polymer in the functional separation surface was 33 mass %. A maximum concentration value of the polymer in the functional separation surface was 36 mass % and the minimum value thereof was 29 mass %. The maximum value and minimum value fell within the range of an average concentration±15%. The variation was small. The ratio of the average concentration of the polymer in the functional separation surface and the content of the polymer in the separation membrane was 183.

The LDH activity was as good as 13 [Δabs/hr/m²].

The amount of elution was evaluated. As a result, the absorbance after the treatment apparatus was prepared was 0.030 and the absorbance after storage at 60° C. for one month was 0.039, which satisfied a standard value of 0.1 or less.

Comparative Example 1

A blood processing apparatus was obtained in the same manner as in Example 1 except that a 60 mass % aqueous dimethylacetamide solution not containing the polymer was used as the bore liquid.

Air bubbles disappeared within one minute. Thus, air-bleeding was satisfactory. However, since the polymer was not contained, LDH activity was 398 [Δabs/hr/m²]. Significant platelet adhesion was observed.

The amount of elution was evaluated. As a result, the absorbance after the treatment apparatus was prepared was 0.034 and the absorbance after storage at 60° C. for one month was 0.133, which was beyond the standard value of 0.1. It was confirmed that the apparatus had no storage stability.

Comparative Example 2

A blood processing apparatus was obtained in the same manner as in Example 1 except that a spinning dope containing a polysulfone (P-1700, manufactured by Solvay S.A.) (17 parts by mass) and dimethylacetamide (special-grade reagent, Kishida Chemical Co., Ltd.) (83 parts by mass) was used and a bore liquid, which was prepared by dissolving poly(hydroxypropyl methacrylate) in a 60 mass % aqueous dimethylacetamide solution so as to obtain a concentration of 0.1 mass % was used.

Five minutes or more was required until air bubbles disappeared. Thus, air-bleeding was unsatisfactory.

The content of the polymer in the separation membrane was 0.50 mass %, and the average concentration of the polymer in the functional separation surface was 73 mass %. A maximum concentration value of the polymer in the functional separation surface was 84 mass % and the minimum value thereof was 64 mass %. The maximum value and minimum value fell within the range of an average concentration±15%. The variation was small. The ratio of the concentration of the polymer in the functional separation surface to the content of the polymer in the separation membrane was 146.

The LDH activity was 398 [Δabs/hr/m²]. Significant platelet adhesion was observed.

The amount of elution was evaluated. As a result, the absorbance after the treatment apparatus was prepared was 0.007 and the absorbance after storage at 60° C. for one month was 0.010, which satisfied a standard value of 0.1 or less.

Comparative Example 3

A blood processing apparatus was obtained in the same manner as in Example 1 except that a bore liquid prepared by dissolving poly(hydroxypropyl methacrylate) in a 60 mass % aqueous dimethylacetamide solution so as to obtain a concentration of 0.1 mass % was used, the spinning rate was set at 40 m/minute and the draft was set at 1.15.

Air bubbles disappeared within three minutes. The air-bleeding was evaluated as "Δ."

The content of the polymer in the separation membrane was 0.33 mass %, and the average concentration of the polymer in the functional separation surface was 28 mass %. A maximum concentration value of the polymer in the functional separation surface was 42 mass % and the minimum value thereof was 10 mass %. The maximum value and minimum value were outside the range of an average concentration±15%. The variation was large. The ratio of the average concentration of the polymer in the functional separation surface and the content of the polymer in the separation membrane was 85.

The LDH activity was as good as 33 [Δ abs/hr/n12].

The amount of elution was evaluated. As a result, the absorbance after the treatment apparatus was prepared was 0.029 and the absorbance after storage at 60° C. for one month was 0.069, which satisfied a standard value of 0.1 or less.

Comparative Example 4

A blood processing apparatus was obtained in the same manner as in Example 1 except that a bore liquid prepared by dissolving poly(hydroxypropyl methacrylate) in a 75 mass % aqueous dimethylacetamide solution so as to obtain a concentration of 0.1 mass % was used, the spinning rate was set at 40 m/minute and the draft was set at 1.15.

Air bubbles disappeared within three minutes. The air-bleeding was evaluated as "Δ."

The content of the polymer in the separation membrane was 0.29 mass %, and the average concentration of the polymer in the functional separation surface was 13 mass %.

A maximum concentration value of the polymer in the functional separation surface was 19 mass % and the minimum value thereof was 3 mass %. The maximum value and minimum value fell within the range of an average concentration±15%. The variation was small. The ratio of the average concentration of the polymer in the functional separation surface and the content of the polymer in the separation membrane was 45.

The LDH activity was 348 [Δ abs/hr/m$^2$]. Significant platelet adhesion was observed.

The amount of elution was evaluated. As a result, the absorbance after the treatment apparatus was prepared was 0.039 and the absorbance after storage at 60° C. for one month was 0.088, which satisfied a standard value of 0.1 or less.

Comparative Example 5

Poly(hydroxyethyl methacrylate) was obtained as follows.

In a flask, ethanol (2600 g) was placed. Under a nitrogen atmosphere, hydroxyethyl methacrylate (Light Ester HO, manufactured by Kyoeisha Chemical Co., Ltd.) (2600 g) was added while stirring. Subsequently, Peroyl IPP (manufactured by NOF Corporation) (7 g) was added. Stirring was continued for 6 hours while controlling the temperature of the reaction solution to be 60° C. After 6 hours, water was added to terminate the reaction. The reaction product was dried under reduced pressure to obtain poly(hydroxyethyl methacrylate). The solubility of poly(hydroxyethyl methacrylate) in water (100 g) was 0.7 g and the weight average molecular weight thereof was 110,000.

A blood processing apparatus was obtained in the same manner as in Example 1 except that a bore liquid prepared by dissolving poly(hydroxyethyl methacrylate) in a 15 mass % aqueous dimethylacetamide solution so as to obtain a concentration of 0.05 mass % was used, the spinning rate was set at 40 m/minute and the draft was set at 1.15.

Air bubbles disappeared within three minutes. The air-bleeding was evaluated as "Δ."

The content of poly(hydroxyethyl methacrylate) in the separation membrane was 0.20 mass % and the average concentration of poly(hydroxyethyl methacrylate) in the functional separation surface was 16 mass %. The maximum concentration value of poly(hydroxyethyl methacrylate) in the functional separation surface was 25 mass % and the minimum value thereof was 8 mass %. The maximum value and minimum value fell within the range of an average concentration±15%. The variation was small. The ratio of the average concentration of poly(hydroxyethyl methacrylate) in the functional separation surface to the content of poly(hydroxyethyl methacrylate) in the separation membrane was 80.

The LDH activity was 329 [Δ abs/hr/m$^2$]. Significant platelet adhesion was observed.

The amount of elution was evaluated. As a result, the absorbance after the treatment apparatus was prepared was 0.031 and the absorbance after storage at 60° C. for one month was 0.145, which was beyond the standard value of 0.1. It was confirmed that the apparatus had no storage stability.

Comparative Example 6

The polymer described in Example 1 was used.
A polysulfone (P-1700, manufactured by Solvay S.A.) (17 parts by mass), a polyvinylpyrrolidone (K-90, manufactured by BASF SE) (4 parts by mass), poly(hydroxypropyl methacrylate) (0.5 parts by mass) and dimethylacetamide (special-grade reagent, manufactured by Kishida Chemical Co., Ltd.) (78.5 parts by mass) was blended to prepare a spinning dope.

As a bore liquid, a 60 mass % aqueous dimethylacetamide solution not containing the polymer was used.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.91. After washed with water and dried, a hollow separation membrane was obtained. Herein, water-washing was performed at a temperature of 90° C. for 180 seconds. The amounts of spinning dope and bore liquid ejected were controlled such that the thickness of the membrane after dry became 35 μm and the inner diameter became 185 μm.

From the obtained separation membrane, a module having an effective membrane area of 1.5 m$^2$ was assembled and sterilized by application of an electron beam to obtain a blood processing apparatus.

Five minutes or more was required until air bubbles disappeared. Thus, air-bleeding was unsatisfactory.

The content of the polymer in the separation membrane was 0.98 mass %, and the average concentration of the polymer in the functional separation surface was 21 mass %. A maximum concentration value of the polymer in the functional separation surface was 26 mass % and the minimum value thereof was 17 mass %. The maximum value and minimum value fell within the range of an average concentration±15%. The variation was small. The ratio of the average concentration of the polymer in the functional separation surface and the content of the polymer in the separation membrane was 21.

The LDH activity was as good as 15 [Δ abs/hr/m$^2$].

The amount of elution was evaluated. As a result, the absorbance after the treatment apparatus was prepared was 0.030 and the absorbance after storage at 60° C. for one month was 0.038, which satisfied a standard value of 0.1 or less.

Comparative Example 7

The spinning dope described in Example 1 was used.
As a bore liquid, a 60 mass % aqueous dimethylacetamide solution not containing the was used.

From a tube-in-orifice type spinneret, the spinning dope and the bore liquid were ejected. At the time of ejection, the temperature of the spinning dope was 40° C. The ejected spinning dope was fed through a portion (drop portion) covered with a hood, soaked in a coagulation bath of 60° C. and coagulated therein. At this time, a spinning rate was set at 30 m/minute. A draft was 0.91. After washed with water and dried, a hollow separation membrane was obtained. Herein, water-washing was performed at a temperature of 90° C. for 180 seconds. The amounts of spinning dope and bore liquid ejected were controlled such that the thickness of the membrane after dry became 35 μm and the inner diameter became 185 μm.

From the obtained separation membrane, a module having an effective membrane area of 1.5 m$^2$ was assembled.

Poly(hydroxyethyl methacrylate) described in Example 6 was dissolved in a 40 mass % aqueous solution of ethanol so as to obtain a concentration of 0.2 mass % to prepare a coating liquid. The coating liquid (500 mL) was injected from a header cap having a nozzle for introducing (ejecting) a liquid at a 200 mL/minute. Excessive solution was removed by use of compressed air. Thereafter, drying was made under reduced pressure until a constant amount was obtained. After completion of drying, an electron beam was applied for sterilization to obtain a blood processing apparatus.

Five minutes or more was required until air bubbles disappeared. Thus, air-bleeding was unsatisfactory.

The content of the polymer in the separation membrane was 0.60 mass %, and the average concentration of the polymer in the functional separation surface was 55 mass %. The maximum concentration value of the polymer in the functional separation surface was 73 mass % and the minimum value thereof was 38 mass %. The maximum value and minimum value were outside the range of an average concentration±15%. The variation was large. The ratio of the average concentration of the polymer in the functional separation surface to the content of the polymer in the separation membrane was 92.

The LDH activity was as good as 13 [Δ abs/hr/m²].

The amount of elution was evaluated. As a result, the absorbance after the treatment apparatus was prepared was 0.031 and the absorbance after storage at 60° C. for one month was 0.040, which satisfied a standard value of 0.1 or less.

Comparative Example 8

In place of the polymer, poly(hydroxyethyl acrylate) (PHEA, manufactured by Scientific Polymer Product) was used. The solubility of poly(hydroxyethyl acrylate) in water (100 g) was 5 g or more and the weight average molecular weight thereof was 260,000.

A blood processing apparatus was obtained in the same manner as in Example 1 except that a bore liquid prepared by dissolving poly(hydroxyethyl acrylate) in a 60 mass % aqueous dimethylacetamide solution so as to obtain a concentration of 0.1 mass %.

Air bubbles disappeared within one minute. Thus, air-bleeding was satisfactory.

The content of poly(hydroxyethyl acrylate) in the separation membrane was 0.40 mass % and the average concentration of poly(hydroxyethyl acrylate) in the functional separation surface was 45 mass %. The maximum concentration value of poly(hydroxyethyl acrylate) in the functional separation surface was 51 mass % and the minimum value thereof was 42 mass %. The maximum value and minimum value fell within the range of an average concentration±15%. The variation was small. The ratio of the average concentration of poly(hydroxyethyl acrylate) in the functional separation surface to the content of poly(hydroxyethyl acrylate) in the separation membrane was 113.

The LDH activity was 378 [Δ abs/hr/m²]. Significant platelet adhesion was observed.

The amount of elution was evaluated. As a result, the absorbance after the treatment apparatus was prepared was 0.042 and the absorbance after storage at 60° C. for one month was 0.140, which was beyond the standard value of 0.1. It was confirmed that the apparatus had no storage stability.

Comparative Example 9

As the polymer having a hydroxy group at an end, polyethylene glycol (PEG, manufactured by Wako Pure Chemical Industries, Ltd.) was used. The solubility of polyethylene glycol in water (100 g) was 5 g or more and the weight average molecular weight thereof was 560,000.

A blood processing apparatus was obtained in the same manner as in Example 1 except that a bore liquid prepared by dissolving polyethylene glycol in a 60 mass % aqueous dimethylacetamide solution so as to obtain a concentration of 0.1 mass %.

Air bubbles disappeared within one minute. Thus, air-bleeding was satisfactory.

The content of polyethylene glycol in the separation membrane was 0.33 mass % and the average concentration of polyethylene glycol in the functional separation surface was 41 mass %. The maximum concentration value of polyethylene glycol in the functional separation surface was 48 mass % and the minimum value thereof was 37 mass %. The maximum value and minimum value fell within the range of an average concentration±15%. The variation was small. The ratio of the average concentration of polyethylene glycol in the functional separation surface to the content of polyethylene glycol in the separation membrane was 124.

The LDH activity was 384 [Δ abs/hr/m²]. Significant platelet adhesion was observed.

The amount of elution was evaluated. As a result, the absorbance after the treatment apparatus was prepared was 0.034 and the absorbance after storage at 60° C. for one month was 0.110, which was beyond the standard value of 0.1. It was confirmed that the apparatus had no storage stability.

Comparative Example 10

In place of the polymer, Styleze 2000 (manufactured by ISP) was used. Styleze 2000 is a copolymer constituted of vinylpyrrolidone, an acrylic acid and lauryl methacrylate. Since suspended insoluble matter in water was not successfully filtered out, it was impossible to measure the solubility in water (100 g). The weight average molecular weight was 980,000.

A blood processing apparatus was obtained in the same manner as in Example 1 except that a bore liquid prepared by dissolving Styleze 2000 in a 60 mass % aqueous dimethylacetamide solution so as to obtain a concentration of 0.1 mass %.

Air bubbles disappeared within one minute. Thus, air-bleeding was satisfactory.

The content of Styleze 2000 in the separation membrane was 0.42 mass % and the average concentration of the polymer in the functional separation surface was 49 mass %. The maximum concentration value of Styleze 2000 in the separation membrane was 54 mass % and the minimum value thereof was 42 mass %. The maximum value and minimum value fell within the range of an average concentration±15%. The variation was small. The ratio of the average concentration of Styleze 2000 in the functional separation surface to the content of Styleze 2000 in the separation membrane was 117.

The LDH activity was as good as 23 [Δ abs/hr/m²].

The amount of elution was evaluated. As a result, the absorbance after the treatment apparatus was prepared was 0.046 and the absorbance after storage at 60° C. for one month was 0.105, which was beyond the standard value of 0.1. It was confirmed that the apparatus had no storage stability.

Comparative Example 11

In place of the polymer, poly(vinyl pyrrolidone-vinyl acetate) (manufactured by Wako Pure Chemical Industries, Ltd.) was used. The solubility of poly(vinyl pyrrolidone-vinyl acetate) in water (100 g) was 2.1 g and the weight average molecular weight thereof was 51,000.

A blood processing apparatus was obtained in the same manner as in Example 1 except that a bore liquid prepared by dissolving poly(vinyl pyrrolidone-vinyl acetate) in a 60 mass % aqueous dimethylacetamide solution so as to obtain a concentration of 0.1 mass % was used.

Air bubbles disappeared within one minute. Thus, air-bleeding was satisfactory.

The content of poly(vinyl pyrrolidone-vinyl acetate) in the separation membrane was 0.37 mass % and the average concentration of poly(vinyl pyrrolidone-vinyl acetate) in the functional separation surface was 36 mass %. The maximum concentration value of poly(vinyl pyrrolidone-vinyl acetate) in the functional separation surface was 46 mass % and the minimum value thereof was 30 mass %. The maximum value and minimum value fell within the range of an average concentration±15%. The variation was small. The ratio of the average concentration of poly(vinyl pyrrolidone-vinyl acetate) in the functional separation surface to the content of poly(vinyl pyrrolidone-vinyl acetate) in the separation membrane was 97.

The LDH activity was as good as 28 [Δ abs/hr/m$^2$].

The amount of elution was evaluated. As a result, the absorbance after the treatment apparatus was prepared was 0.058 and the absorbance after storage at 60° C. for one month was 0.133, which was beyond the standard value of 0.1. It was confirmed that the apparatus had no storage stability.

Comparative Example 12

Poly(hydroxyethyl methacrylate) described in Comparative Example 5 was used.

A blood processing apparatus was obtained in the same manner as in Example 1 except that a bore liquid prepared by dissolving poly(hydroxyethyl acrylate) in a 60 mass % aqueous dimethylacetamide solution so as to obtain a concentration of 10 mass % was used.

Five minutes or more was required until air bubbles disappeared. Thus, air-bleeding was unsatisfactory.

The content of poly(hydroxyethyl methacrylate) in the separation membrane was 32 mass %, and the average concentration of poly(hydroxyethyl methacrylate) in the functional separation surface was 100 mass %. The maximum concentration value of poly(hydroxyethyl methacrylate) in the functional separation surface was 100 mass % and the minimum value was 98 mass %. The maximum value and minimum value fell within the range of an average concentration±15%. The variation was small. The ratio of the average concentration of poly(hydroxyethyl methacrylate) in the functional separation surface to the content of poly(hydroxyethyl methacrylate) in the separation membrane was 3.

The LDH activity was 268 [Δ abs/hr/m$^2$]. Significant platelet adhesion was observed.

The amount of elution was evaluated. As a result, the absorbance after the treatment apparatus was prepared was 0.044 and the absorbance after storage at 60° C. for one month was 0.055, which was beyond the standard value of 0.1. It was confirmed that the apparatus had no storage stability.

TABLE 1

|  | Example 1 | Example 2 | Example 3 | Example 4 | Example 5 | Example 6 | Example 7 |
|---|---|---|---|---|---|---|---|
| Polysulfone polymer | PS | PS | PS | PES | PS | PS | PS |
| Hydrophilic polymer | PVP | PVP | PVP | PVP | VA64 | PVP | PVP |
| Polymer having a hydroxy group | Poly(hydroxypropyl methacrylate) PHPMA | Poly(hydroxyethyl methacrylate) PHEMA | Poly(hydroxyethyl methacrylate) PHEMA | Poly(hydroxypropyl methacrylate) PHPMA | Poly(hydroxypropyl methacrylate) PHPMA | Poly(hydroxyethyl methacrylate) PHEMA | Poly(hydroxybutyl methacrylate) PHBMA |
| Solubility | less than 0.1 g | less than 0.1 g | less than 0.1 g | less than 0.1 g | less than 0.1 g | less than 0.1 g | less than 0.1 g |
| Weight average molecular weight (Mw) | 330,000 | 1,700,000 | 1,700,000 | 330,000 | 330,000 | 200,000 | 380,000 |
| Added to | Bore liquid | Bore liquid | Bore liquid | Bore liquid | Bore liquid | Bore liquid | Bore liquid |
| Addition concentration | 0.03 mass % (300 ppm) | 0.01 mass % (100 ppm) | 0.1 mass % (1000 ppm) | 0.03 mass % (300 ppm) | 0.03 mass % (300 ppm) | 0.05 mass % (500 ppm) | 0.03 mass % (300 ppm) |
| Draft | 0.91 | 0.91 | 0.91 | 0.98 | 0.95 | 0.95 | 0.91 |
| Content [A] of polymer | 0.19 mass % | 0.11 mass % | 0.60 mass % | 0.20 mass % | 0.16 mass % | 0.48 mass % | 0.18 mass % |
| Average surface concentration [B] of polymer | 34 mass % | 21 mass % | 83 mass % | 36 mass % | 49 mass % | 48 mass % | 33 mass % |
| Maximum value | 41 mass % | 22 mass % | 90 mass % | 46 mass % | 57 mass % | 58 mass % | 36 mass % |
| Minimum value | 30 mass % | 20 mass % | 79 mass % | 30 mass % | 43 mass % | 33 mass % | 29 mass % |
| [B]/[A] | 179 | 191 | 138 | 180 | 306 | 100 | 183 |
| Air-bleeding | ○ | ○ | ○ | ○ | ○ | ○ | ○ |
| LDH activity | 14 | 12 | 16 | 19 | 21 | 18 | 13 |
| UV value at t = 0 | 0.041 | 0.035 | 0.032 | 0.039 | 0.034 | 0.033 | 0.030 |
| UV value after one month at 60° C. | 0.044 | 0.041 | 0.040 | 0.046 | 0.039 | 0.040 | 0.039 |

TABLE 2

|  | Comparative Example 1 | Comparative Example 2 | Comparative Example 3 | Comparative Example 4 | Comparative Example 5 | Comparative Example 6 |
|---|---|---|---|---|---|---|
| Polysulfone polymer | PS | PS | PS | PS | PS | PS |
| Hydrophilic polymer | PVP | — | PVP | PVP | PVP | PVP |
| Polymer having a hydroxy group | — | Poly(hydroxypropyl methacrylate) PHPMA | Poly(hydroxypropyl methacrylate) PHPMA | Poly(hydroxypropyl methacrylate) PHPMA | Poly(hydroxyethyl methacrylate) PHEMA | Poly(hydroxypropyl methacrylate) PHPMA |
| Solubility | — | less than 0.1 g | less than 0.1 g | less than 0.1 g | 0.7 g | less than 0.1 g |
| Weight average molecular weight (Mw) | — | 330,000 | 330,000 | 330,000 | 110,000 | 330,000 |
| Added to | — | Bore liquid | Bore liquid | Bore liquid | Bore liquid | Dope |
| Addition concentration | — | 0.1 mass % (1000 ppm) | 0.1 mass % (1000 ppm) | 0.1 mass % (1000 ppm) | 0.05 mass % (500 ppm) | 0.5 mass % |
| Draft | 0.91 | 0.91 | 1.15 | 1.15 | 1.15 | 0.91 |
| Content [A] of polymer | — | 0.50 mass % | 0.33 mass % | 0.29 mass % | 0.20 mass % | 0.98 mass % |
| Average surface concentration [B] of polymer | — | 73 mass % | 28 mass % | 13 mass % | 16 mass % | 21 mass % |
| Maximum value | — | 84 mass % | 42 mass % | 19 mass % | 25 mass % | 26 mass % |
| Minimum value | — | 64 mass % | 10 mass % | 3 mass % | 8 mass % | 17 mass % |
| [B]/[A] | — | 146 | 85 | 45 | 80 | 21 |
| Air-bleeding | ○ | X | Δ | Δ | Δ | X |
| LDH activity | 398 | 393 | 33 | 348 | 329 | 15 |
| UV value at t = 0 | 0.034 | 0.007 | 0.029 | 0.039 | 0.031 | 0.030 |
| UV value after one month at 60° C. | 0.133 | 0.010 | 0.069 | 0.088 | 0.145 | 0.038 |

TABLE 3

|  | Comparative Example 7 | Comparative Example 8 | Comparative Example 9 | Comparative Example 10 | Comparative Example 11 | Comparative Example 12 |
|---|---|---|---|---|---|---|
| Polysulfone polymer | PS | PS | PS | PS | PS | PS |
| Hydrophilic polymer | PVP | PVP | PVP | PVP | PVP | PVP |
| Polymer having a hydroxy group | Poly(hydroxypropyl methacrylate) PHPMA | Poly(hydroxyethyl acrylate) PHEA | Polyethylene glycol PEG | Styleze2000 | Poly(vinyl pyrrolidone-vinyl acetate) | Poly(hydroxyethyl methacrylate) PHEMA |
| Solubility | less than 0.1 g | 5 g or more | 5 g or more | Unmeasurable | 2.1 g | 0.7 g |
| Weight average molecular weight (Mw) | 200,000 | 260,000 | 560,000 | 980,000 | 51,000 | 110,000 |
| Added to | Coating liquid | Bore liquid | Bore liquid | Bore liquid | Bore liquid | Bore liquid |
| Addition concentration | 0.2 mass % (2000 ppm) | 0.1 mass % (1000 ppm) | 0.1 mass % (1000 ppm) | 0.1 mass % (1000 ppm) | 0.1 mass % (1000 ppm) | 10 mass % |
| Draft | 0.91 | 0.91 | 0.91 | 0.91 | 0.91 | 0.91 |
| Content [A] of polymer | 0.60 mass % | 0.40 mass % | 0.33 mass % | 0.42 mass % | 0.37 mass % | 32 mass % |
| Average surface concentration [B] of polymer | 55 mass % | 45 mass % | 41 mass % | 49 mass % | 36 mass % | 100 mass % |
| Maximum value | 73 mass % | 51 mass % | 48 mass % | 54 mass % | 46 mass % | 100 mass % |
| Minimum value | 38 mass % | 42 mass % | 37 mass % | 42 mass % | 30 mass % | 98 mass % |
| [B]/[A] | 92 | 113 | 124 | 117 | 97 | 3 |
| Air-bleeding | X | ○ | ○ | ○ | ○ | X |
| LDH activity | 13 | 378 | 384 | 23 | 28 | 268 |
| UV value at t = 0 | 0.031 | 0.042 | 0.034 | 0.046 | 0.058 | 0.044 |
| UV value after one month at 60° C. | 0.040 | 0.140 | 0.110 | 0.105 | 0.133 | 0.055 |

The present application is based on a Japanese patent application (Japanese Patent Application No. 2011-242260) filed on Nov. 4, 2011, the content of which is incorporated herein by reference.

INDUSTRIAL APPLICABILITY

The present invention can provide a separation membrane for blood processing having not only excellent substance removal performance but also blood compatibility as well as storage stability, also with satisfactory air-bleeding during priming treatment of the separation membrane for blood processing, and provide a blood processing apparatus having the membrane installed therein. Therefore, the present invention has industrial applicability as a separation membrane to be used in an extracorporeal-circulation blood purification therapy.

The invention claimed is:

1. A hollow-fiber separation membrane for blood processing comprising
   a polysulfone polymer,
   a hydrophilic polymer and
   a polymer having a hydroxy group in a side chain and having a solubility of 0.5 g or less in 100 g of water at 20° C., wherein
   the content of the polymer in the hollow-fiber separation membrane is 0.11 to 0.6 mass %;

the average concentration of the polymer in a functional separation surface of the hollow-fiber separation membrane is 20 mass % or more, and a maximum value and a minimum value of the polymer concentration in the functional separation surface fall within the range of (the average concentration of the polymer in the functional separation surface)±15%;

the average concentration of the polymer in the functional separation surface relative to the content of the polymer in the hollow-fiber separation membrane is 100 times or more; and the polymer having a hydroxy group in a side chain is a polymer obtained by polymerizing only an acrylate monomer and/or methacrylate monomer having a hydroxy group in a side chain or polymerizing so as to partly contain such a monomer.

2. The hollow-fiber separation membrane for blood processing according to claim 1, wherein the hollow-fiber separation membrane is sterilized by radiation.

3. The hollow-fiber separation membrane for blood processing according to claim 1, wherein the hydrophilic polymer is polyvinylpyrrolidone.

4. The hollow-fiber separation membrane for blood processing according to claim 1, wherein the polysulfone polymer is at least one selected from the group consisting of polysulfone, polyethersulfone, polyphenylenesulfone, polyarylethersulfone and a copolymer of these.

5. The hollow-fiber separation membrane for blood processing according to claim 1, wherein the polymer having a hydroxy group in a side chain is a polymer obtained by polymerizing only an acrylate monomer and/or methacrylate monomer having a hydroxy group in a side chain.

6. The hollow-fiber separation membrane for blood processing according to claim 1, wherein the polymer having a hydroxy group in a side chain has a weight average molecular weight of 200,000 or more.

7. The hollow-fiber separation membrane for blood processing according to claim 1, wherein the inner diameter of the hollow-fiber membrane is 180 to 220 μm.

8. The hollow-fiber separation membrane for blood processing according to claim 7, wherein the thickness of the hollow-fiber separation membrane is 50 μm or less.

9. The hollow-fiber separation membrane for blood processing according to claim 1, wherein the hollow-fiber membrane is formed by a spinning process in which a draft ratio is 0.95 or less.

10. The hollow-fiber separation membrane for blood processing according to claim 1, wherein the average concentration of the polymer in the functional separation surface of the separation membrane is from 20 mass % to 49 mass %.

11. The hollow-fiber separation membrane for blood processing according to claim 1, wherein the inner diameter of the hollow-fiber membrane is 170 to 250 μm.

12. The hollow-fiber separation membrane for blood processing according to claim 1, wherein the hollow-fiber membrane is formed by a spinning process in which a draft ratio is 1 or less.

13. A blood processing apparatus in which the hollow-fiber separation membrane for blood processing according to claim 1 is installed.

* * * * *